United States Patent [19]

Griffin et al.

[11] Patent Number: 5,084,274

[45] Date of Patent: Jan. 28, 1992

[54] INHIBITION OF ARTERIAL THROMBOTIC OCCLUSION OR THROMBOEMBOLISM

[75] Inventors: John H. Griffin; Andras Gruber, both of San Diego; Stephen R. Hanson, Encinitas; Lawrence A. Harker, San Diego, all of Calif.

[73] Assignee: Scripps Clinic and Research Foundation, La Jolla, Calif.

[21] Appl. No.: 121,702

[22] Filed: Nov. 17, 1987

[51] Int. Cl.$^5$ .................. A61K 57/547; C12N 9/64
[52] U.S. Cl. .................. 424/94.64; 424/94.63; 514/21; 514/8; 514/12; 435/215; 435/216; 435/217; 435/226
[58] Field of Search .............. 514/8, 12, 21; 435/226, 435/215, 216, 217, 69.6; 424/94.64, 94.63

[56] References Cited

U.S. PATENT DOCUMENTS 4,568,544  2/1986  Hasegawa et al. .
4,775,624  10/1988  Bang et al. .................. 435/226

OTHER PUBLICATIONS

Verstraete et al., (1985) The Lancet, pp. 842-847.

Primary Examiner—Garnette D. Draper
Assistant Examiner—R. Keith Baker
Attorney, Agent, or Firm—Morgan & Finnegan

[57] ABSTRACT

The method of preventing arterial thrombotic occulsion or thromboembolism by administering plasma-derived or recombinate produced protein C alone or in combination with a thrombolytic agent or combinations of thrombolytic agents.

36 Claims, 8 Drawing Sheets

INHIBITION OF ARTERIAL THROMBOTIC OCCLUSION OR THROMBOEMBOLISM

BACKGROUND OF THE INVENTION

This invention relates to the inhibition of arterial thrombotic occlusion or thromboembolism by plasma-derived or recombinant produced activated protein C (APC) alone or in combination with a thrombolytic agent.

Many of the surgical procedures carry the risk of venous and arterial thrombosis and thromboembolism. Application of current anti-platelet or fibrinolytic drugs in intraoperative or postoperative cases could lead to serious bleeding complications. Thus, the use of these agents requires extra precaution. Even in diseases complicated with arterial thrombosis, the use of antithrombotic and/or thrombolytic therapy has undesired side effects, such as bleeding or reocclusion during thrombolytic treatment in myocardial infarction, bleeding or thrombosis following surgery, and thrombosis following surgery that employs grafts or other cardiovascular prosthetic devices.

Therefore, there is a need for an antithrombotic therapy which would be anticoagulant, anti-platelet and fibrinolytic at the same time without the hazards of hemorrhage. APC is unique among the physiologic anticoagulants since it inhibits coagulation and stimulates fibrinolysis. APC inhibits the thrombin mediated activation of platelets as well as the formation of fibrin, and thus, the formation of arterial thrombus built up mostly by platelets and fibrin. The use of APC reduces the dose of tissue-type plasminogen activator (t-PA) or other thrombolytic agents by its actions. Thus, APC provides safer thrombolysis with less risk of bleeding and less risk of reocclusion.

APC is a potent anticoagulant enzyme in vitro and in vivo. APC inhibits the blood coagulation pathways and the formation of thrombin by proteolytic cleavage of F.Va and F.VIIIa, and also enhances fibrinolysis (Seegers et al., *Thrombosis Res.*, 1, 443–460 (1972); Kisiel, *J. Clin. Invest.*, 64, 761–769 (1979); Marlar & Griffin, *J. Clin. Invest.*, 66, 1186–1189 (1980); Marlar et al., *Blood*, 59, 1067–1072 (1982); Clouse & Comp, *New Engl. J. Med.*, 314, 1298–1304 (1986)). APC is generated from its circulating precursor, namely from the vitamin K dependent protein C (PC), upon activation by immobilized thrombin on the endothelium of blood vessels (Mammen et al., *Thromb. Diath. Haemorrh.*, 5, 218–249 (1960); Stenflo, *J. Biol. Chem.*, 251, 355–363 (1976); Esmon & Owen, *Proc. Natl. Acad. Sci. USA*, 78, 2249–2252 (1981)). APC, through the protein C pathway, serves as the enzyme central to the negative feedback regulation of coagulation. Inherited deficiency in PC is associated with venous thromboembolic diseases (Griffin et al., *J. Clin. Invest.*, 68, 1370–1373 (1981); Bertina et. al., *Thromb. Haemost.*, 48, 1–5 (1982); Griffin, Seminars in Thrombosis and Hemostasis, 10, 162–166 (1984); Marciniak et al., *Blood*, 65, 15–20 (1985)), but inherited protein C deficiency is not significantly associated with arterial thrombosis (Coller et al., *Arteriosclerosis*, 7, 456–462 (1987). Infusion of APC decreases blood coagulability in various animal models and prevents the coagulopathic and lethal effects in E.coli infusion in baboons (Comp & Esmon, *J. Clin. Invest.*, 68, 1221–1228 (1981); Comp et al., *J. Clin. Invest.*, 70, 127–134 (1982); Colucci et al., *J. Clin. Invest.*, 74, 200–204 (1984); Taylor et al., *J. Clin. Invest.*, 79, 918–925 (1987); Burdick & Schaub, *Thrombosis Res.*, 45, 413–419 (1987)). Infusion of a thrombolytic agent like t-PA into humans results in effective thrombolysis in acute myocardial infarction (AMI) (Yusuf et al., *European Heart Journal*. 6, 556–585 (1985); European Cooperative Study Group, *Lancet.*, 842–847 (1985)).

SUMMARY OF THE INVENTION

The present invention comprises a method of inhibiting in a patient acute arterial thrombotic occlusion, thromboembolism, or stenosis in coronary, cerebral or peripheral arteries or in vascular grafts which comprises administering to said patient an effective amount of plasma-derived or recombinant produced activated protein C alone or in combination with a thrombolytic agent such as tissue plasminogen activator or its analogs, urokinase or its analogs, prourokinase or its analogs, streptokinase or its analogs, an acylated form of plasminogen or plasmin or their analogs and acylated streptokinase plasminogen complex.

BRIEF DESCRIPTION OF THE DRAWINGS

A more complete appreciation of the present invention and many of the attendant advantages thereof will be readily obtained as the invention becomes better understood by reference to the following detailed description in connection with the accompanying drawings, wherein all figures refer to the effects of infusion of APC alone or APC and a thrombolytic agent into baboons used for an arterial thrombosis model:

FIGS. 1a thru 3a show the effect of infusions of low dose APC on the clotting of blood measured using activated partial thromboplastin time assays (APTTs).

FIGS. 4a and 5a show the effect of infusions of high dose APC on APTTs.

FIGS. 6a and 7a show the effect of infusions of a combination of APC and t-PA on APTTs.

FIGS. 1b thru 5b show the effect of APC and FIGS. 6b and 7b of APC plus t-PA on blood flow and bleeding time.

FIGS. 1c thru 5c show the effect of APC infusion or APC plus t-PA infusion (FIGS. 6c and 7c) on platelet deposition (i.e. thrombus formation) in a Dacron graft from analyses of radioimaging data of radiolabeled platelets.

DETAILED DESCRIPTION OF THE INVENTION

The Thrombosis Model

An arterial thrombosis model has been tested and characterized in previous experiments (Hanson & Harker, *J. Clin. Invest.*, 75, 1591–1599 (1985); Hanson & Harker, *Thromb. Haemostas.*, 53, 423–427 (1985); Hanson et al., *Arteriosclerosis*, 5, 595–603 (1985)). This model is useful in judging the effect of drugs on arterial thrombus formation. Male baboons weighing 10–12 kg were dewormed and observed for more than 40 days at our animal facility prior to the experiments. Permanent arteriovenous shunts were prepared between the femoral artery and vein using 3 mm i.d. Silastic tubing Subsequent interposition of 5 cm long, 4 mm i.d. Dacron vascular grafts served as thrombogenic surface, inducing continuous platelet-fibrin thrombus formation until progressive occlusion of the graft at 70±20 min. Experimental results using recombinant produced APC in the baboon in this arterial thrombosis model in baboons were obtained that indicate similar results to the plasma-derived APC.

Administration of APC and t-PA

All baboons underwent at least one control experiment prior to APC administration. The APC was given by injecting one-fourth to one-third of the total PC dose as a bolus and the remaining three-fourths to two-thirds of the dose as continuous infusion for one hour. The interposition of the graft and bolus injection were made at time=0 and APC was administered at the proximal site of the Silastic shunt. The experiments were divided into three groups; the "low dose" APC group received 2.0-3.4 mg (total), the "high dose" APC group received 11 mg (total), and the combination group received 2.1 mg APC plus 1.3 mg t-PA (total).

Preparation of APC

Human plasma prothrombin complex concentrate (Immuno AG, Vienna) was the source of protein C. A monoclonal antibody directed against the light chain of PC (designated C3) was prepared and coupled to CNBromide activated Sepharose 4B (Pharmacia, Uppsala, Sweden), and the prothrombin complex concentrate diluted in a buffer (0.02 M/l Tris, 0.002 M/l EDTA; 0.002 M/l Benzamidine; 0.1 M/l NaCl, 0.075 mM/l pAPMSF, 0.02% Na-azide, 0.02% Tween 20; pH 7.4 was applied on the column. The PC was eluted with 2 M thiocyanate and dialyzed against Tris-buffered saline (0.01 M/l Tris; 0.14 M/l NaCl, pH 7.4). Purified PC was activated using thrombin-Sepharose beads as described in Marlar et al., *Blood*, 59, 1067-1072 (1982).

The purified APC appeared on SDS-PAGE as two bands and no significant contamination (≧5%) by other proteins was detected. In some preparations, the trace amounts of thrombin verified by clotting assay were separated by using either Bio-Rex 70 absorption or Fast Protein Liquid Chromatography (FPLC) chromatography on a Mono-Q column (Pharmacia, Uppsala, Sweden. The activity of the purified APC was measured in activated partial thromboplastin time (APTT) clotting assays (Marlar et al., *Blood*, 59, 1067-1072 (1982)) that measured anticoagulant activity and in chromogenic substrate assays, and results were compared to the activity of a previously purified APC preparation and to the activity of APC generated by addition of the PC activator, Protac (American Diagnostica, Greenwich, Conn.), to normal human plasma.

Amidolytic and Anticoagulant Assays of Purified APC

Various amounts (0.5 to 5 microliters) of APC solution or of reference purified APC solution (0.5 mg/ml) were added to 210 microliters of buffer containing 0.01 M Tris-HCl, 0.14 M NaCl, 1% ovalumbin, 0.02% sodium azide, 0.05% Tween-80, pH 8.0 and the samples were placed in microtiter plate wells (Corning, Dynatech--Immulon, or Costar). After addition of 20 microliters of chromogenic substrate, S-2401 (4.6 mM), the change in absorbance of the sample was read using an ELISA plate reader at room temperature. The amidolytic activity of the APC was determined by comparing the observed values to the reference values. The anticoagulant activity was determined using the APTT assay. In this assay, dilutions of normal human plasma (nhp) were made using protein C deficient plasma (pcdp) as diluent. 100 microliters of these mixtures was mixed with 100 microliters of Protac reagent (American Diagnostica) and 100 microliters of APTT reagent (General Diagnostics). After 5 min incubation, 100 microliters of $CaCl_2$ (50 mM) was added and the clotting time determined. Since nhp contains 4.0 micrograms/ml of protein C, the activity of unknown APC solutions was determined by comparison to the standard curves obtained for dilutions of nhp. In some experiments, standard curves for the amidolytic activity of APC were made using dilutions of nhp activated by Protac. In some experiments, S-2366 was used in place of S-2401. The specific activity of all preparations of APC was in good agreement with values for APC based on protein content determined by absorbance at 280 nm using an extinction coefficient of 1.4 per cm per mg/ml.

The doses of APC described here in the baboon experiments indicate the functional activity of the APC preparations in comparison to normal human plasma and purified APC as standards. The purified APC preparations showed an anticoagulant effect on human and baboon Plasmas using the APTT assay, and cleaved chromogenic oligo peptide-paranitroanilide substrates, S-2366 and S-2401 (Kabi, Stockholm, Sweden) in a concentration dependent manner. t-PA from a melanoma cell line was kindly provided by Dr. Desire Collen (Leuven, Belgium).

Studies for Establishing the Antithrombotic Properties of APC in Arterial Thrombosis

Blood Flow in the Shunt

The blood flow was measured using a Doppler flow meter fitted around the distal segment of the Silastic tubing. The values were given in ml/min and were in the range of 100-200 ml/min (equal to 13.3-26.5 cm/sec velocity) providing arterial flow conditions. The flow values were recorded at regular intervals throughout the experiments. The method was described in Hanson & Harker et al., *Arteriosclerosis*, 5, 595-603 (1985).

Platelet Deposition in the Dacron Graft

The deposition of $^{111}$In-labeled Platelets was detected by scintillation camera images of the graft. The platelet labeling methods and data analysis were the same as described in Hanson & Harker, *Thromb. Haemostas.*, 53, 423-427 (1985) with the only modification that the equation was simplified for the number of platelets in the graft as follows:

$$\frac{\text{cpm-graft} \times \text{platelet count/ml}}{\text{cmp/ml of whole blood}}$$

The duration of imaging also was extended to two hours from the time (t=0) of initiating the graft and the APC bolus in the APC experiments. Since platelet accumulation usually reached a plateau in control experiments within one hour, this one hour period was not exceeded with imaging the inhibition of platelet deposition. Inhibition of platelet deposition in treated animals was expressed as % of total number of platelets deposited in the control experiments at 30 and 60 minutes timepoints. The equations for the calculation of inhibition are shown in Table I. Since platelet deposition depends on platelet count (Harker & Hanson, *Thromb. Haemostas.*, 53, 423-427 (1985), correction of inhibition of platelet deposition was made using the equation given in Table 1.

Bleeding Times

Standardized template bleeding times were performed on the shaved volar surface of the forearm before and during the experiment as described in Malpass et al., *Blood,* 57, 736-740 (1981), with two incisions, 5 mm long, 1 mm deep each, at 40 mm Hg inflation of the sphygmomanometer.

Tests for Anticoagulant Effects and for In Vivo Plasma Levels of APC

Anticoagulant effect of APC infusion was measured by Performing APTT assays at regular intervals from arterial blood drawn into sodium citrate. The test was done within 5 to 10 minutes from sampling in order to minimalize the in vitro inhibition of APC by plasma Protein C inhibitor(s). To determine the circulating APC levels a chromogenic amidolytic assay was developed. ELISA microtiter plates (Dynatech-Immunlon or Costar) were coated with the anti-protein C monoclonal antibody, C3, that does not influence the amidolytic activity of the enzyme significantly. Blood was drawn into 3.8% citrate, 4.6% benzamidine solution (9:1), and the plasma obtained after immediate centrifugation was kept on −80° C. until studied. 10 microliters of this plasma sample was diluted to 160-200 microliters with a Tris-buffered saline containing 1% BSA as carrier and a 0.36% benzamidine as enzyme inhibitor and was incubated for one hour at 37° C. in the antibody coated wells. The solution was removed and the wells washed to remove unbound constituents and the benzamidine. Then a chromogenic substrate, either S-2366 or S-2401, was added and the rate of cleavage of the substrate was measured spectrophotometrically. Using standard APC dilutions, the APC concentration in the plasma samples was calculated from the calibration curve.

Results Indicating the APC is Antithrombotic Under Arterial Flow Conditions

FIGS. 1a thru 3a show the APTT prolongation in the "low dose" experiments (open circles). 2.0-3.4 mg total dose of human APC approximately doubled the APTT values on an average. After termination of the APC infusion (vertical arrow), the APTT values progressively decreased and the measured level of APC as based on amidolytic activity decreased (solid line) suggesting a circulation half life of 12-16 minutes. FIGS. 4a and 5a show the effect of "high dose" APC on APTTs. Administration of 11 mg APC resulted in a 3-4 times prolongation in APTT in both experiments. The pattern of APTT changes and the measured level of APC after termination of the infusion indicate similar half-life values of APC (approximately 12 min) for these higher dose of APC. Combination of APC (2.1 mg) and t-PA (1.3 mg) had the same effect on APTTs as the low dose APC had alone (FIGS. 6a and 7a). In none of the experiments was the APTT decreased to the starting value (at 0 min) at the end of the observation (at 120 min).

The same figures (FIGS. 1a thru 7a) demonstrate the changes in the APC levels measured by the chromogenic assay described above (closed circles). An overall range of 0.38 to 0.70 micrograms/ml of APC plasma concentration in the "low dose" experiments (FIGS. 1a thru 3a), 0.94 to 1.64 micrograms/ml in the "high dose" experiments (FIGS. 4a and 5a) and 0.30 to 0.90 micrograms/ml in the combination experiments (FIGS. 6a and 7a) were measured. The circulation half life of APC in the baboons determined in amidolytic activity assays was similar to that determined from the APTT determinations, regardless of the total dose of the APC enzyme. The in vivo circulating APC levels did not entirely return to the starting values within two hours. The five fold difference in APC doses used in high dose compared to low dose experiments did not result in five-fold higher circulating APC levels, suggesting an efficient clearance or temporary storage mechanism or receptor mediated regulation for APC.

In six of the seven experiments the bleeding times remained in the normal range (FIGS. 1b and 3b thru 7b vertical segments) with a slight average elevation. In one of the "low dose" experiments the bleeding times were prolonged and abnormal (FIG. 2b), both before and during and after the experiment. Since the bleeding time was abnormally long in this animal before the APC infusion, the long bleeding time observed during APC infusion was not due to APC. These results suggest that circulating APC at the doses employed does not significantly alter the hemostatic platelet function measured by standardized bleeding time techniques. There were no suffusions, hematomas or rebleeding observed at tissue injury sites (i.e. sewing cuffs) typical of higher doses of t-PA.

Figure 1:
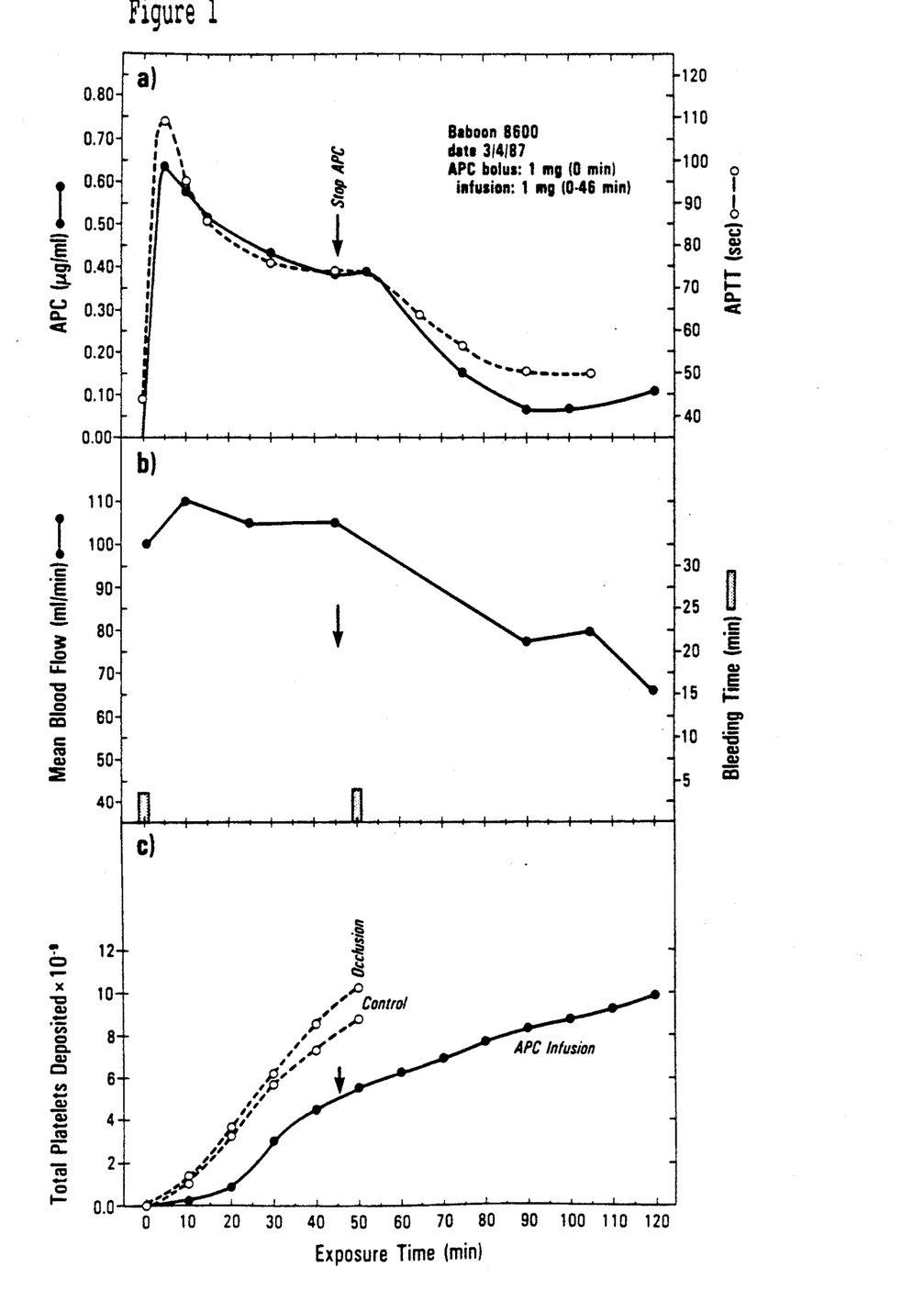
Figure 2:
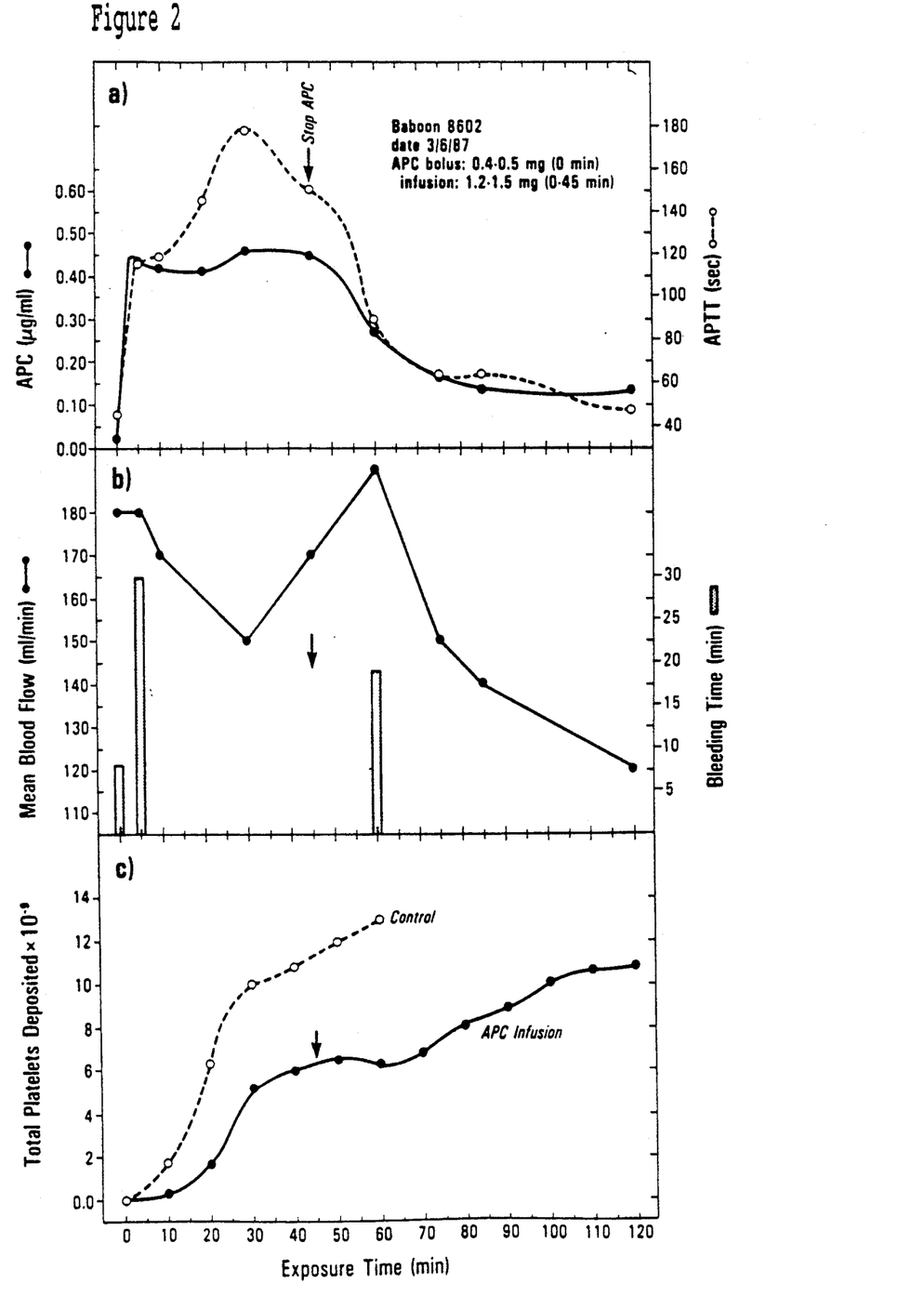
Figure 3:
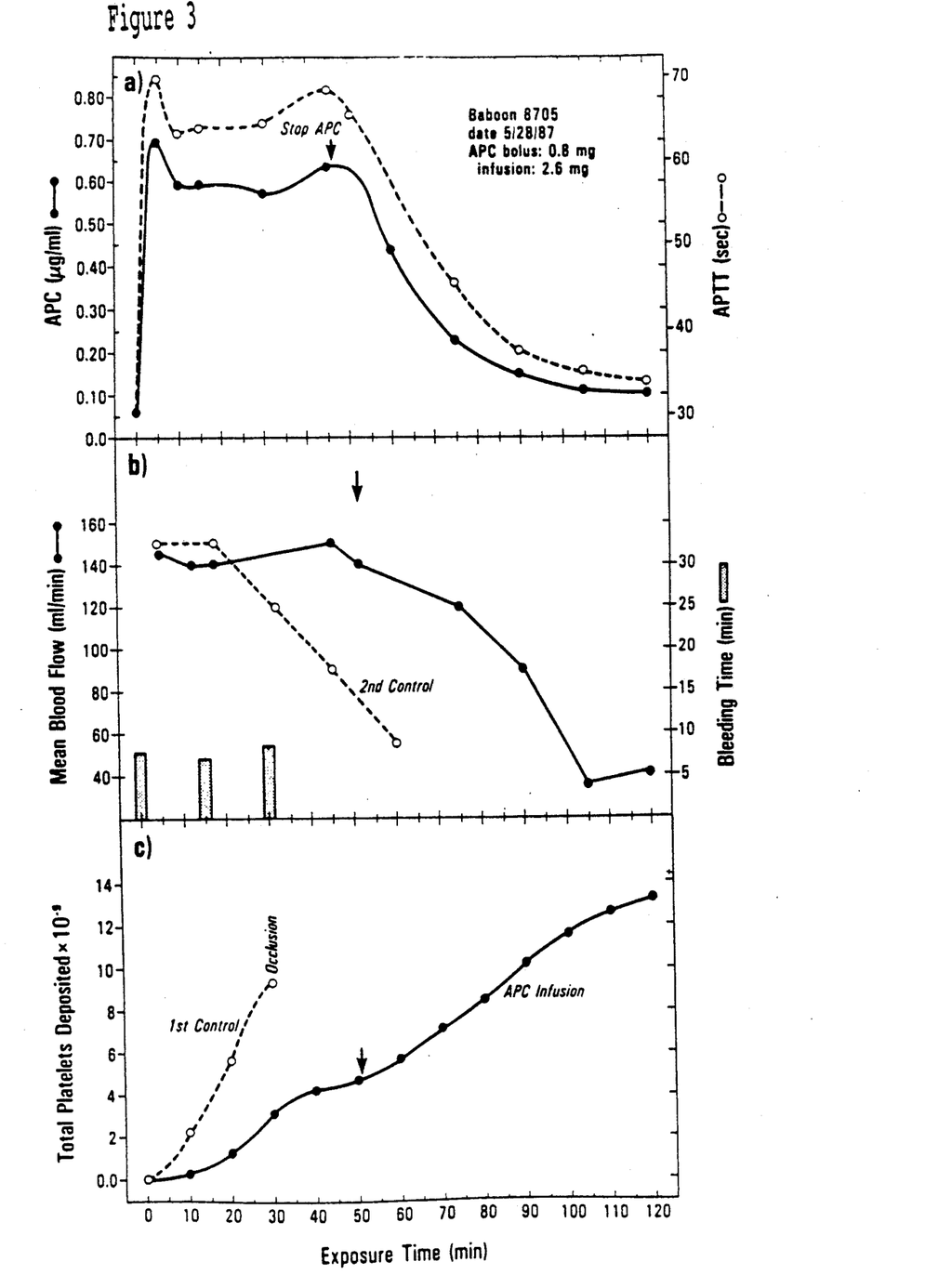
Figure 4:
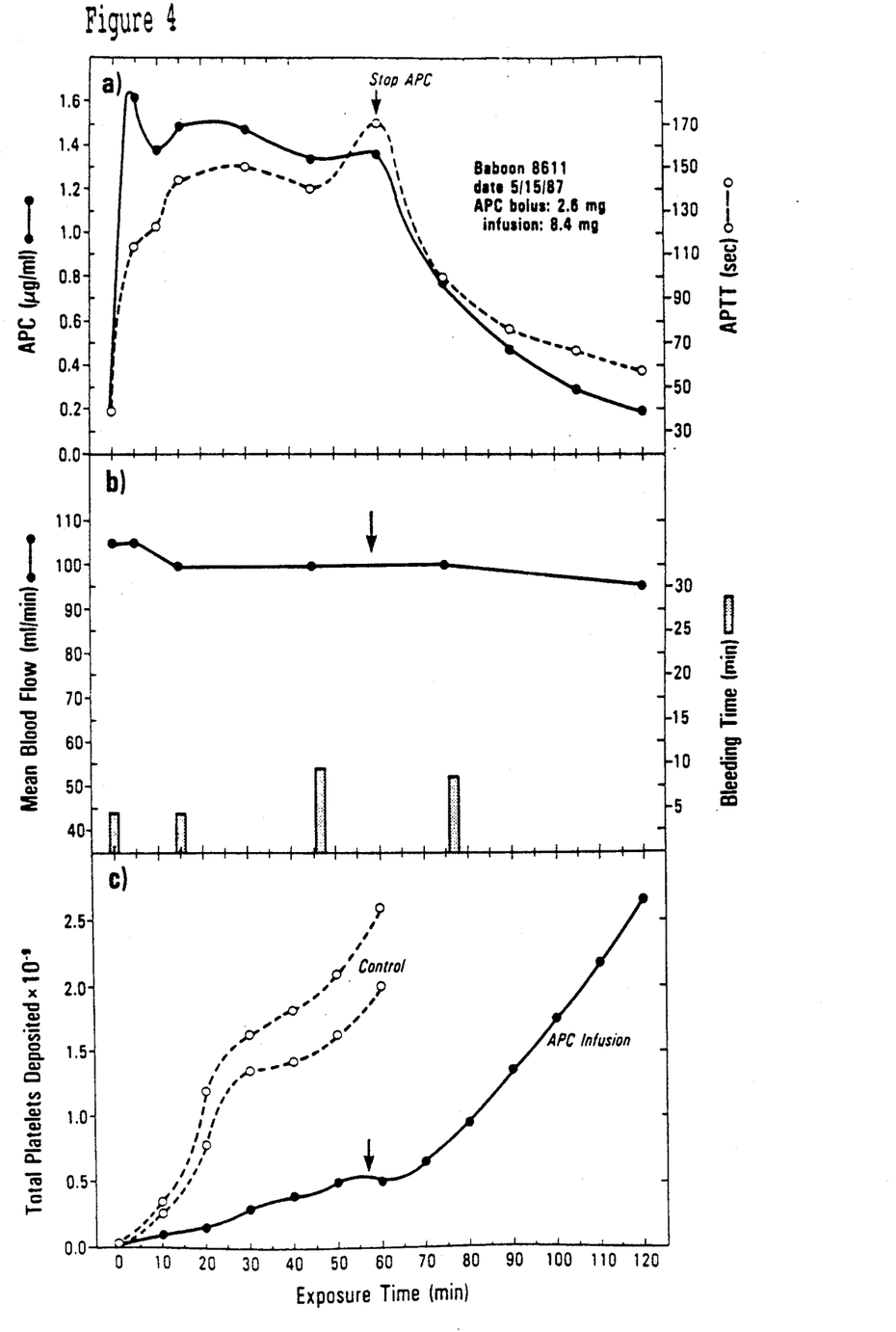
Figure 5:
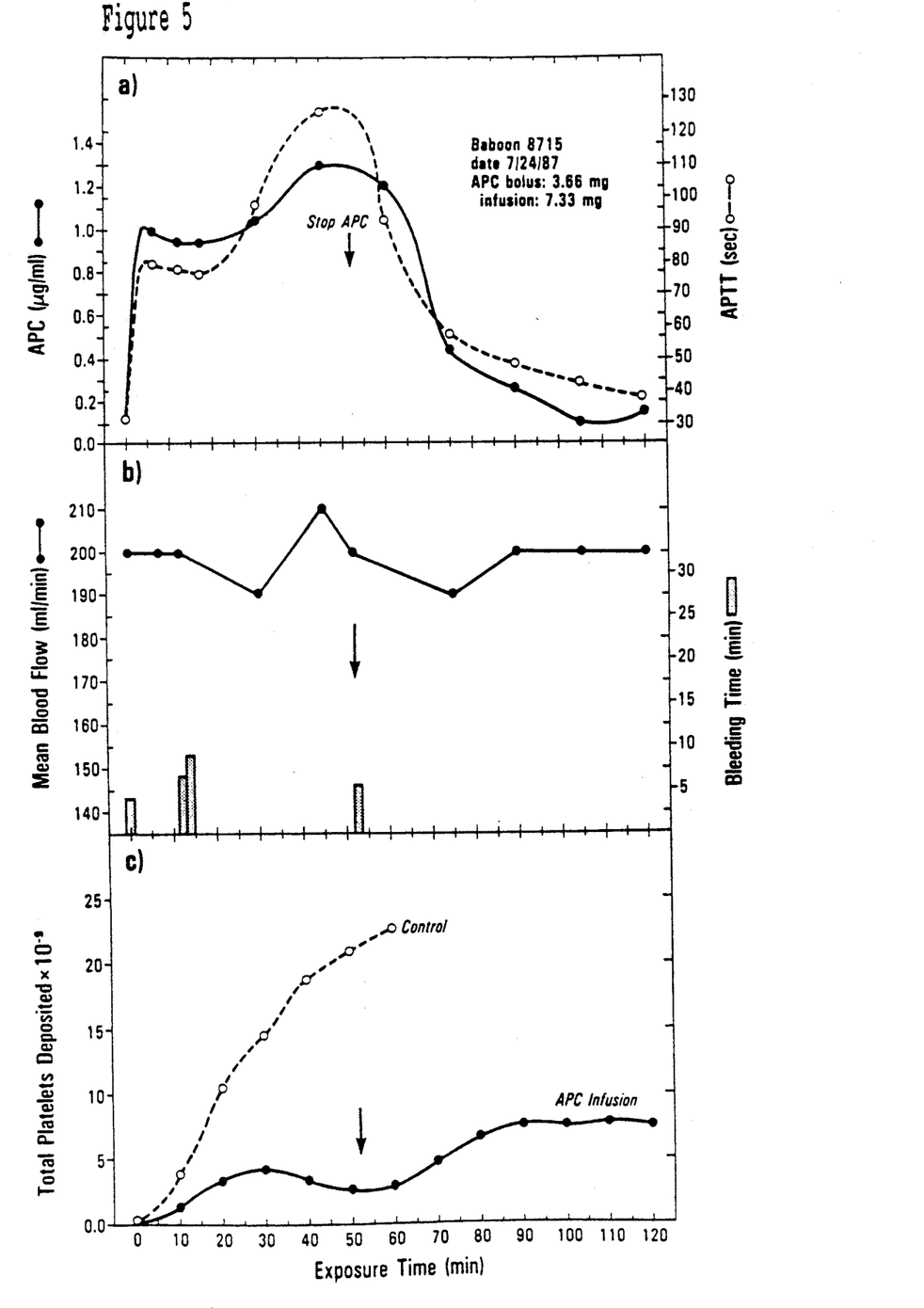
Figure 6:
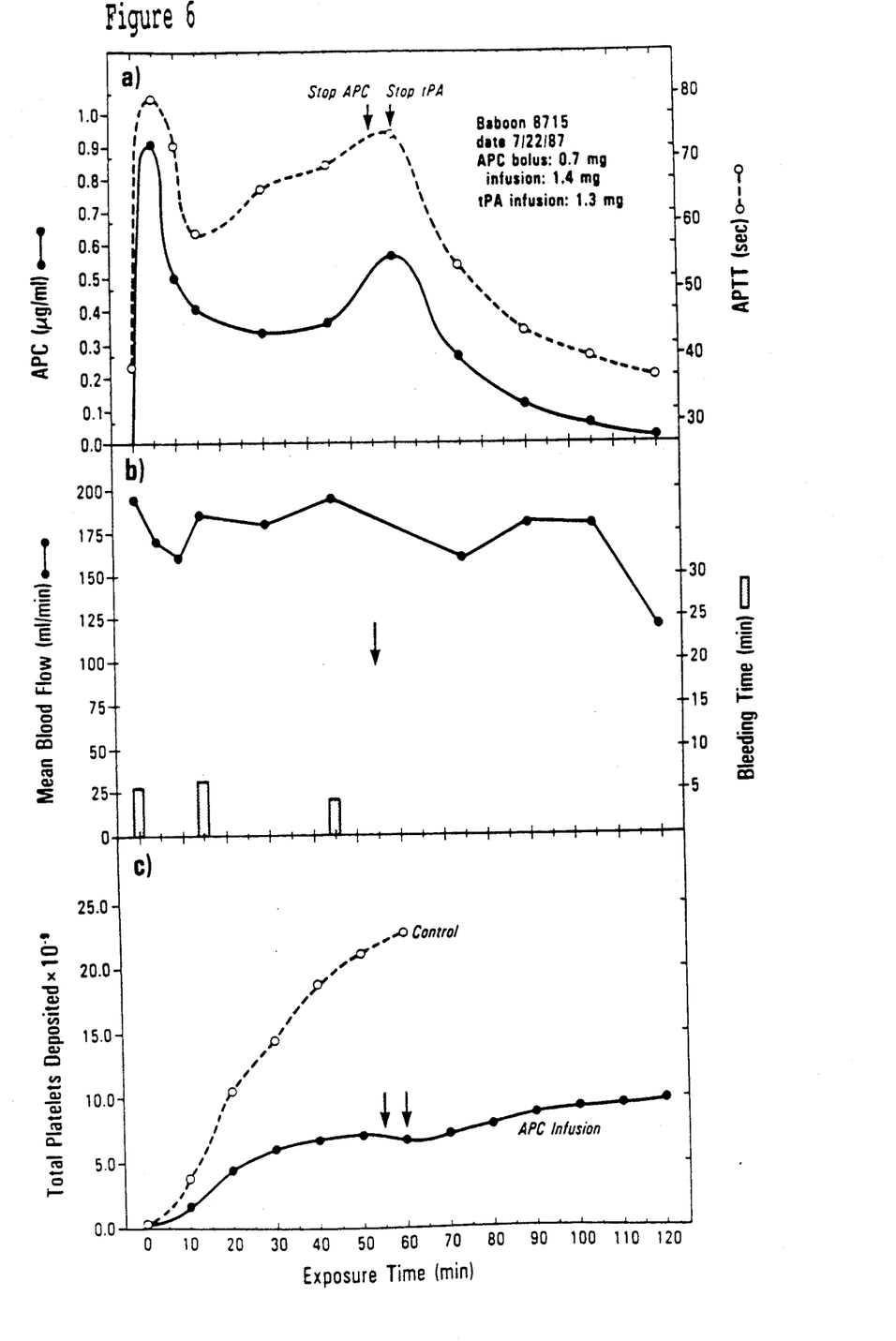
Figure 7:
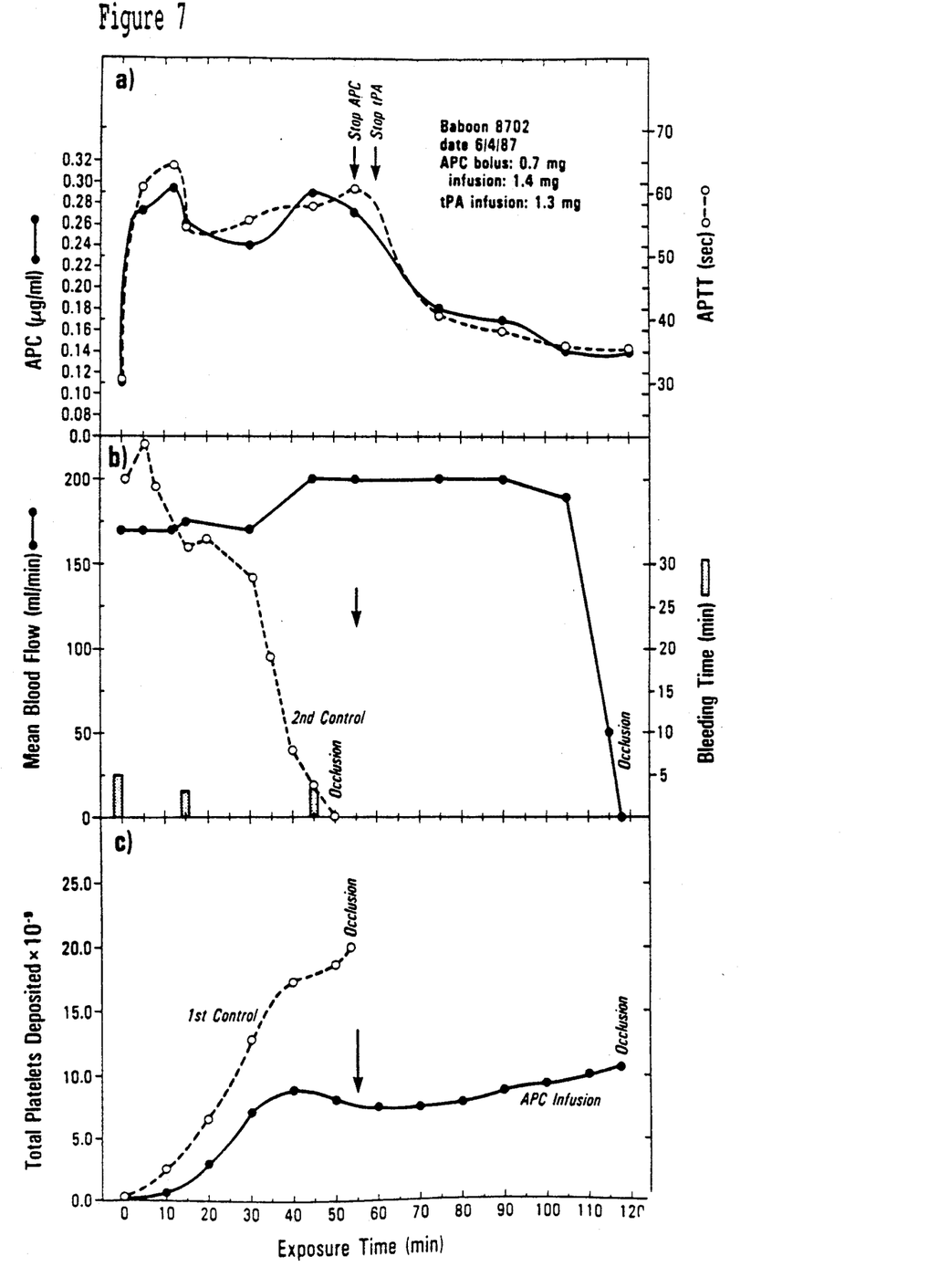

The blood flow was maintained undiminished in the experiments during APC administration (FIGS. 1b thru 7b, solid circles) in contrast to control experiments for the same animals were occlusion regularly occurred. Six of the seven grafts remained open throughout the whole observation period with good arterial flow. In one of the APC-t-PA experiments (FIG. 6b) the Dacron graft failed at 115 minutes. In four of the nine control studies the grafts occluded within one hour, and these grafts fail in 70±20 minutes when there is no effective antithrombotic agent in the circulation. The blood flow changes in two control experiments are demonstrated in FIG. 3b and FIG. 7b. FIG. 3b shows the flow rates of the second control, when the graft remained open up to 1 hr (the first graft became occluded). In FIG. 7b rapid progressive occlusion of the control graft can be observed. These data showed that APC alone or in combination with t-PA is antithrombotic under arterial flow conditions. The high dose APC experiments showed long lasting antithrombotic effects since the flow did not change significantly throughout two hours.

Figure 8:
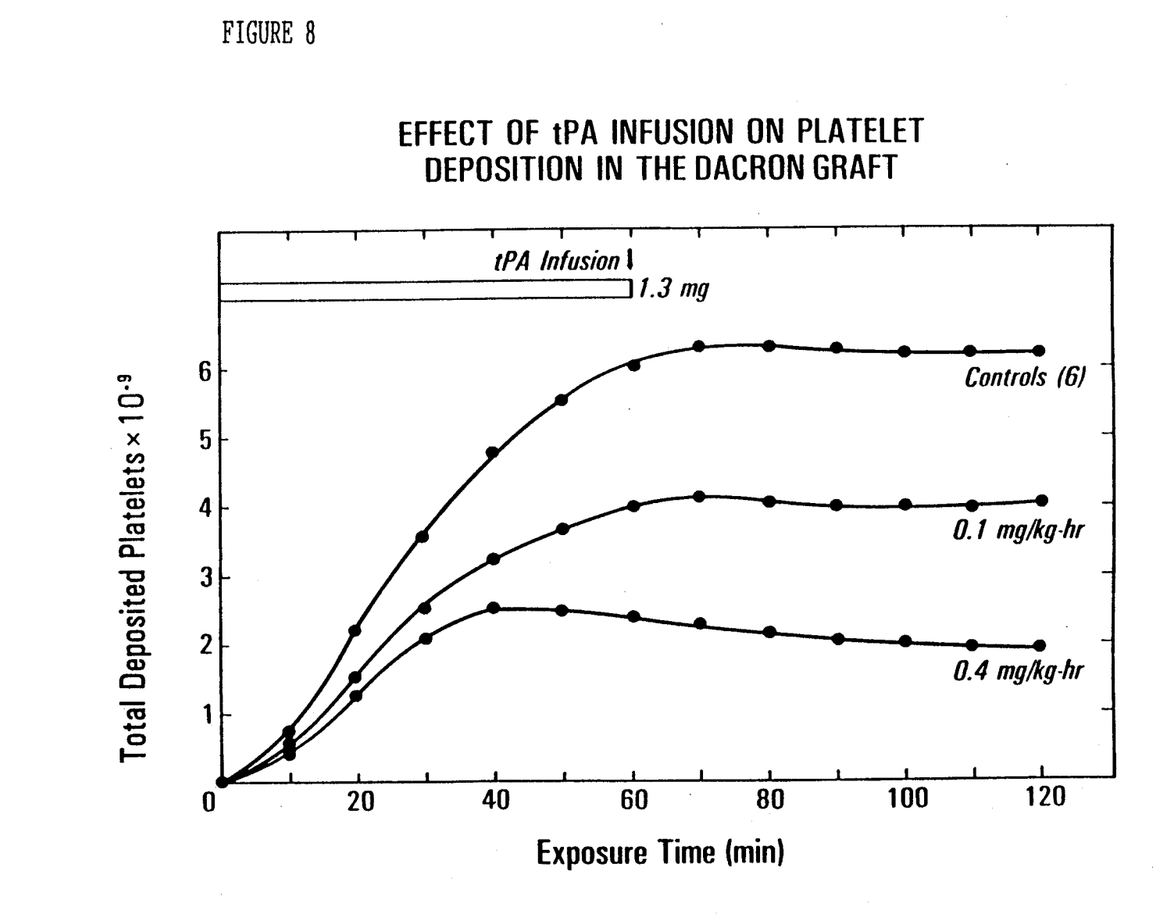
FIG. 8 shows the effect of t-PA infusion on platelet deposition (i.e. thrombus formation) in a Dacron graft from analyses of radioimaging data of radiolabeled platelets.

FIGS. 1c thru 7c show the results of analyses of radioimaging data. The values express the total platelets deposited in the Dacron graft for a maximum of one hour in the control and two hours in the APC experiments. Solid circles (—) show the number of platelets deposited in arterial thrombus formation when APC was infused while open circles (----) show the results for control experiments done in the same animals. The typical sigmoid curve can be seen in the controls as described in Hanson & Harker, *Thromb. Haemostas.,* 423-427 (1985). The deposition of platelets in the graft was significantly inhibited in every APC or APC-t-PA experiment, compared to controls. The degree of inhibition was given in percentage in Table I. The corrected values for inhibition of platelet deposition ($I_2$, Table 1) were 34%, 52% and 42% in the "low dose" experiments at 30 min, respectively (mean: 43%). (FIGS. 1c thru 3c). In the "high dose" experiments the values were 74% and 64% at 30 min (mean: 69%) and 72% and 83% at 60 min (mean: 78%) (FIGS. 4c and 5c) and the APC-t-PA experiments 53% and 36% at 30 min (mean: 45%) (FIGS. 6c and 7c). A long-lasting inhibition of platelet deposition was seen in the high dose studies after terminating APC infusion. FIG. 8 shows the results of some previous studies with t-PA in the same experimental model. 1 mg of t-PA (0.1 mg/kg/hour) infusion had an intermediate antiplatelet effect in these experiments.

Our results provide evidence that human APC inhibits arterial thrombus information in a dose dependent manner and that combination of APC with t-PA inhibits arterial thrombus formation. This shows that APC infusion could reduce the antithrombotic dose of t-PA. These effects of APC are achieved without a significant prolongation of the bleeding time and without risks of bleeding.

Advantage

Human APC infusion alone or in combination with a thrombolytic agent (t-PA) can be used as a therapeutic agent in humans with arterial thrombosis. The results of the studies provide evidence that APC is a very potent antithrombotic agent under arterial flow conditions at plasma levels of 0.24 to 1.6 micrograms/ml.

From the experiments it can be concluded that APC alone or APC in combination with a thromobolytic agent is a markedly effective antithrombotic agent for complex thrombus formation under arterial flow conditions.

APC alone or a combination of APC with a thrombolytic agent such a t-PA potently inhibits the participation of both platelets and fibrin formation in acute arterial thrombosis of a complex type, a process that is unresponsive to heparin or currently available antiplatelet drugs when used alone or in combination. Since the APC is a physiologic material, its administration has potent antithrombotic effects without causing significant impairment of primary hemostasis (as measured in bleeding time tests) or evident toxicity.

Application

Therapy using APC alone or APC in combination with a thrombolytic agent is useful for vascular disorders involving arterial thrombosis.

Some examples of arterial thrombosis where APC alone or in combination with a thrombolytic agent is useful include the following clinical settings.

1. Acute arterial thrombotic occlusion including coronary, cerebral or peripheral arteries.

2. Acute thrombotic occlusion or restenosis after angioplasty.

3. Reocclusion or restenosis after thrombolytic therapy. Thrombolytic agents such as t-PA salvage ischemic tissue when used within hours of acute heart attack or stroke by re-establishing blood flow in the occluded artery. At present, between one-four and one-third of patients who have successful thrombolytic reperfusion of occluded coronary arteries subsequently undergo reocclusion after discontinuing t-PA infusion. This complication occurs despite full-dose heparin therapy. APC will have greater efficacy than heparin in preventing reocclusion.

4. Small and large caliber vascular graft occlusion. Vascular grafts of small caliber, i.e., 3-/mm diameter, have a high frequency of thrombotic occlusion. APC alone or in combination with a thrombolytic agent is useful to Prevent occlusion.

5. Hemodialysis. The prosthetic surfaces and flow design of all hemodialyzers are thrombogenic. Currently heparin is infused during dialysis. However, heparin is only partially effective, thereby limiting the reuse of dialyzers. Also, heparin has a number of troublesome side effects and complications.

6. Cardiopulmonary bypass surgery. To prevent thrombus formation in the oxygenator and pump apparatus, heparin is currently used. However, it fails to inhibit platelet activation and the resultant transient platelet dysfunction which predisposes to bleeding problems post-operatively.

7. Left ventricular cardiac assist device. This prosthetic pump is highly thrombogenic and results in life threatening thromboembolic events—complications that are only partially reduced by convential anticoagulants (heparin or coumarin drugs).

8. Total artificial heart and left ventricular assist devices.

9. Other arterial thrombosis. APC is useful for arterial thrombosis or thromboembolism where current therapeutic measures are either contraindicated or not effective. For example, APC is useful for the treatment of acute pre-or postcapillary occlusion, including transplantations, retina thrombosis, or microthrombotic necrosis of any organ complicating infections, tumors, or coumarin treatment.

In summary, human APC, a naturally occurring physiologic antithrombotic human protein, is superior to other available antithrombotic drugs in terms of bleeding tendency (heparin, thrombolytic drugs, antiplatelet drugs), toxicity (some antiplatelet drugs), antigenicity (streptokinase), clearance rate (heparin, antiplatelet drugs, teratogenicity (coumarin derivatives), general side effects (antiplatelet drugs), lack of immediate efficacy (antiplatelet drugs, coumarin derivatives), allergic reactions (antiplatelet drugs, streptokinase, heparin), and hypotensive effect (prostacyclin).

APC combined with t-PA or another thrombolytic agent improves the antithrombotic effect of a thrombolytic agent alone. Thus, APC therapy will reduce the doses of t-PA or other thrombolytic agents required for therapeutic treatment of thrombosis, thereby avoiding the complications of high doses of thrombolytic agents.

The above description provides details of the manner in which the embodiments of the present invention may be made and used. This description, while exemplary of the present invention, is not to be construed as specifically limiting the invention and such variations which would be within the purview of one skilled in the art are to be considered to fall within the scope of this invention.

TABLE 1

| | INHIBITION OF GRAFT PLATELET DEPOSITION BY APC/t-PA | | | | | | | |
|---|---|---|---|---|---|---|---|---|
| | Number of Platelets Per Microliter | | Deposited on Graft Platelets × $10^{-9}$ | | | | % Inhibition* | |
| Animal # | Platelet Count × $10^{-3}$ | | Control | | Drug | | Uncorrected = $I_1$ | Corrected = $I_2$ |
| Low Dose APC | Control | Drug | 30' | 60' | 30' | 60' | 30' | 60' | 30' | 60' |
| 87-05 | 445 | 225 | 9.3 | — | 3.1 | 5.8 | 67 | — | 34 | — |
| 86-02 | 415 | 445 | 10.0 | 13.1 | 5.2 | 6.4 | 48 | 51 | 52 | 54 |

TABLE 1-continued

INHIBITION OF GRAFT PLATELET DEPOSITION BY APC/t-PA

| Animal # | Number of Platelets Per Microliter Platelet Count × 10⁻³ | | Deposited on Graft Platelets × 10⁻⁹ | | | | % Inhibition* | | | |
|---|---|---|---|---|---|---|---|---|---|---|
| | | | Control | | Drug | | Uncorrected = $I_1$ | | Corrected = $I_2$ | |
| Low Dose APC | Control | Drug | 30' | 60' | 30' | 60' | 30' | 60' | 30' | 60' |
| 86-00 | 388 | 337 | 6.0 | — | 3.0 | 6.2 | 50 | — | 42 | — |
| | | | | | | Mean: | 55 | 51 | 43 | 54 |
| High Dose APC | | | | | | | | | | |
| 86-11 | 173 | 135 | 1.5 | 2.3 | 0.3 | 0.5 | 80 | 78 | 74 | 72 |
| 87-15 | 429 | 340 | 14.6 | 22.7 | 4.2 | 3.0 | 71 | 87 | 64 | 83 |
| | | | | | | Mean: | 76 | 83 | 69 | 78 |
| APC Plus t-PA | | | | | | | | | | |
| 87-15 | 429 | 380 | 14.6 | 22.7 | 6.1 | 6.7 | 58 | 71 | 53 | 67 |
| 87-02 | 491 | 430 | 12.7 | — | 7.1 | — | 44 | — | 36 | — |
| | | | | | | Mean: | 51 | 71 | 41 | 67 |

*$I_1 = \left(1 - \frac{PD_A}{PD_C}\right) \times 100$, $I_2 = \left(1 - \frac{PD_A}{PD_C} \times \frac{PC_C}{PC_A}\right) \times 100$ PD = Platelet Deposition
PC = Platelet Count
A = APC
C = Control

What is claimed is:

1. A method of inhibiting in a patient acute arterial thrombotic occlusion, thromboembolism, or stenosis in coronary, cerebral or peripheral arteries or in vascular grafts which comprises administering to said patient 0.2 mg/kg/hr. to 1.1 mg/kg/hr. plasma-derived activated protein C alone or in combination with a thrombolytic agent or combinations of thrombolytic agents selected from the group consisting of tissue plasminogen activator, urokinase, prourokinase, streptokinase, acylated form of plasminogen, acylated form of plasmin, and acylated streptokinase-plasminogen complex.

2. A method according to claim 1, wherein said thrombolytic agent is tissue plasminogen activator.

3. A method according to claim 1, wherein said thrombolytic agent is urokinase.

4. A method according to claim 1, wherein said thrombolytic agent is prourokinase.

5. A method according to claim 1, wherein said thrombolytic agent is streptokinase.

6. A method according to claim 1, wherein said thrombolytic agent is an acylated form of plasminogen or plasmin.

7. A method according to claim 1, wherein said thrombolytic agent is acylated streptokinase-plasminogen complex.

8. A method of inhibiting in a patient acute arterial thrombotic occlusion, thromboembolism, or stenosis in coronary, cerebral or peripheral arteries or in vascular grafts which comprises administering to said patient 0.2 mg/kg/hr. to 1.1 mg/kg/hr. recombinant produced activated protein C alone or in combination with a thrombolytic agent or combinations of thrombolytic agents selected from the group consisting of tissue plasminogen activator, urokinase, prourokinase, streptokinase, acylated form of plasminogen, acylated form of plasmin, and acylated streptokinase-plasminogen complex.

9. A method according to claim 8, wherein said thrombolytic agent is tissue plasminogen activator.

10. A method according to claim 8, wherein said thrombolytic agent is urokinase.

11. A method according to claim 8, wherein said thrombolytic agent is prourokinase.

12. A method according to claim 8, wherein said thrombolytic agent is streptokinase.

13. A method according to claim 8, wherein said thrombolytic agent is an acylated form of plasminogen or plasmin.

14. A method according to claim 8, wherein said thrombolytic agent is acylated streptokinase-plasminogen complex.

15. A method of inhibiting in a patient, arterial blockages comprising:
   (A) administering to said patient an effective amount of activated protein C;
   (B) said administration comprising;
      (1) a bolus injection,
      (2) a bolus injection and continuous infusion following said bolus, or
      (3) a continuous infusion;
   (C) controlling said administration to achieve an activated protein C plasma level in the range of 0.1 to 1.6 µg/ml; and further;
   (D) controlling said administration to achieve
      (1) decreased platelet deposition.

16. A method according to claim 15 wherein said activated protein C is plasma-derived.

17. A method according to claim 15 wherein said activated protein C is recombinantly produced.

18. A method of inhibiting in a patient, arterial blockages comprising:
   (A) administering to said patient an effective amount of activated protein C;
   (B) said administration comprising;
      (1) a bolus injection,
      (2) a bolus injection and continuous infusion following said bolus, or
      (3) a continuous infusion;
   (C) controlling said administration to achieve an activated protein C plasma level in the range of 0.1 to 1.6 µg/ml;
   (D) administering an effective amount of tissue plasminogen activator in combination with said activated protein C; and further;
   (E) controlling said administration to achieve
      (1) decreased platelet deposition.

19. A method according to claim 18 wherein said activated protein C is plasma-derived.

20. A method according to claim 18 wherein said activated protein C is recombinantly produced.

21. A method according to claim 18 wherein said tissue plasminogen activator is infused at a dose rate of 0.13 mg/kg-hr.

22. A method according to claim 18 wherein said tissue plasminogen activator is infused at a dose rate of 0.1 to 0.4 mg/kg-hr.

23. A method of inhibiting in a patient, arterial blockages comprising:
   (A) administering to said patient an effective amount of activated protein C;
   (B) said administration comprising;
      (1) a bolus injection,
      (2) a bolus injection and continuous infusion following said bolus, or
      (3) a continuous infusion;
   (C) controlling said administration to achieve an activated protein C plasma level in the range of 0.1 to 1.6 µg/ml;
   (D) administering an effective amount of a thrombolytic agent in combination with said activated protein C; said thrombolytic agent selected from the group consisting of tissue plasminogen activator, urokinase, prourokinase, streptokinase, acylated form of plasminogen, acylated form of plasmin, and acylated streptokinase-plasminogen complex and further;
   (E) controlling said administration to achieve
      (1) decreased platelet deposition.

24. A method according to claim 23 wherein activated protein C is plasma-derived.

25. A method according to claim 23 wherein activated protein C is recombinantly produced.

26. A method of inhibiting arterial platelet deposition in a patient comprising:
   (A) administering to said patient an effective amount of activated protein C;
   (B) said administration comprising;
      (1) a bolus injection,
      (2) a bolus injection and continuous infusion following said bolus, or
      (3) a continuous infusion;
   (C) controlling said administration to achieve an activated protein C plasma level in the range of 0.1 to 1.6 µg/ml; and further;
   (D) controlling said administration to achieve
      (1) decreased platelet deposition.

27. A method according to claim 26 wherein said activated protein C is plasma-derived.

28. A method according to claim 26 wherein said activated protein C is recombinantly produced.

29. A method of inhibiting arterial platelet deposition in a patient comprising:
   (A) administering to said patient an effective amount of activated protein C;
   (B) said administration comprising;
      (1) a bolus injection,
      (2) a bolus injection and continuous infusion following said bolus, or
      (3) a continuous infusion;
   (C) controlling said administration to achieve an activated protein C plasma level in the range of 0.1 to 1.6 µg/ml;
   (D) administering an effective amount of tissue plasminogen activator in combination with said activated protein C; and further;
   (E) controlling said administration to achieve
      (1) decreased platelet deposition.

30. A method according to claim 29 wherein said activated protein C is plasma-derived.

31. A method according to claim 29 wherein said activated protein C is recombinantly produced.

32. A method according to claim 29 wherein said tissue plasminogen activator is infused at a dose rate of 0.13 mg/kg-hr.

33. A method according to claim 29 wherein said tissue plasminogen activator is infused at a dose rate of 0.1 to 0.4 mg/kg-hr.

34. A method of inhibiting arterial platelet deposition in a patient comprising:
   (A) administering to said patient an effective amount of activated protein C;
   (B) said administration comprising;
      (1) a bolus injection,
      (2) a bolus injection and continuous infusion following said bolus, or
      (3) a continuous infusion;
   (C) controlling said administration to achieve an activated protein C plasma level in the range of 0.1 to 1.6 µg/ml; and further;
   (D) administering an effective amount of a thrombolytic agent in combination with said activated protein C; said thrombolytic agent selected from the group consisting of tissue plasminogen activator, urokinase, prourokinase, streptokinase, acylated form of plasminogen, acylated form of plasmin, and acylated streptokinase-plasminogen complex and further;
   (E) controlling said administration to achieve
      (1) decreased platelet deposition.

35. A method according to claim 34 wherein activated protein C is plasma-derived.

36. A method according to claim 34 wherein activated protein C is recombinantly produced.

* * * * *